US007073504B2

(12) United States Patent
Callister et al.

(10) Patent No.: US 7,073,504 B2
(45) Date of Patent: *Jul. 11, 2006

(54) CONTRACEPTIVE SYSTEM AND METHOD OF USE

(75) Inventors: Jeffrey P. Callister, Menlo Park, CA (US); William S. Tremulis, Redwood City, CA (US); Denise S. Harges, Salt Lake, UT (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/770,123

(22) Filed: Dec. 18, 1996

(65) Prior Publication Data

US 2002/0013589 A1   Jan. 31, 2002

(51) Int. Cl.
*A61F 6/06* (2006.01)
(52) U.S. Cl. ...................... 128/831; 128/830
(58) Field of Classification Search ............ 604/96, 604/104, 106–109, 515, 93.01, 96.01, 174–175, 604/264; 606/191–198, 135; 623/1, 1.1, 623/1.11, 1.12, 1.15, 1.22, 902–903; 128/830–831
See application file for complete search history.

(56) References Cited

U.S. PATENT DOCUMENTS

| 3,334,629 | A | 8/1967 | Cohn |
| 3,687,129 | A | 8/1972 | Nuwayser .................. 128/1 R |
| 3,855,996 | A | 12/1974 | Bolduc .......................... 128/1 |
| 4,052,754 | A | 10/1977 | Homsy |
| 4,140,126 | A | 2/1979 | Choudhury |
| 4,185,618 | A | 1/1980 | Corey |

(Continued)

FOREIGN PATENT DOCUMENTS

EP   0 105 669   4/1984

(Continued)

OTHER PUBLICATIONS

T. Schmitz-Rode, MD, et al., "Experimental nonsurgical female sterilization: transcervical implantation of microspindles in fallopian tubes," Journal of Vascular and Interventional Radiology, vol. 5 (No. 6), p. 905-910, (Nov.-Dec. 1994).

(Continued)

*Primary Examiner*—Henry Bennett
*Assistant Examiner*—Andrea M. Ragonese
(74) *Attorney, Agent, or Firm*—Barbara A. Wrigley; Oppenheimer Wolff & Donnelly LLP; José W. Jimenez

(57) ABSTRACT

A device and method of using the device for contraception or sterilization and particularly for reversible contraception by occluding a reproductive lumen to prevent the passage of reproductive cells through the lumen for a desired period of time until the patient wishes to become fertile again and then be reopened. The occluding member preferably comprises a tubular framework formed from a shape memory material configured to be implanted in a reproductive lumen. The occluding member is implanted within a body lumen, secured to the wall of the reproductive lumen and then collapsed to collapse the wall and occlude the lumen. Alternatively, the occluding member may be collapsed upon a solid plug. The closure of the reproductive lumen may be reversed by introducing a balloon catheter and by a series of inflations of the balloon reexpanding the collapsed occluding member or by removing the plug. The occluding member and the plug may be configured to facilitate endothelialization, to provoke an inflammatory responses or to deliver a drug.

72 Claims, 5 Drawing Sheets

U.S. PATENT DOCUMENTS

| | | | |
|---|---|---|---|
| 4,503,569 A | 3/1985 | Dotter | 3/1.4 |
| 4,562,596 A | 1/1986 | Kornberg | |
| 4,579,110 A | 4/1986 | Hamou | |
| 4,595,000 A | 6/1986 | Hamou | |
| 4,606,336 A | 8/1986 | Zeluff | 128/130 |
| 4,638,803 A | 1/1987 | Rand | |
| 4,688,553 A | 8/1987 | Metals | |
| 4,700,701 A | 10/1987 | Montaldi | |
| 4,733,665 A * | 3/1988 | Palmaz | 604/104 |
| 4,787,899 A | 11/1988 | Lazarus | |
| 4,994,069 A | 2/1991 | Ritchart et al. | |
| 5,104,399 A | 4/1992 | Lazarus | |
| 5,147,370 A * | 9/1992 | McNamara | 606/108 |
| 5,163,958 A * | 11/1992 | Pinchuk | 604/194 |
| 5,167,614 A * | 12/1992 | Tessmann et al. | 623/1.15 |
| 5,190,546 A | 3/1993 | Jervis | 606/78 |
| 5,192,301 A | 3/1993 | Kamiya et al. | |
| 5,197,978 A | 3/1993 | Hess | 623/1 |
| 5,226,911 A | 7/1993 | Chee et al. | |
| 5,275,622 A | 1/1994 | Lazarus et al. | |
| 5,303,719 A | 4/1994 | Wilk et al. | 128/898 |
| 5,354,295 A | 10/1994 | Guglielmi et al. | |
| 5,366,472 A * | 11/1994 | Hillstead | 606/194 |
| 5,382,259 A | 1/1995 | Phelps et al. | |
| 5,382,261 A | 1/1995 | Palmaz | 606/158 |
| 5,433,217 A | 7/1995 | Pianetti et al. | |
| 5,456,713 A | 10/1995 | Chuter | |
| 5,474,089 A | 12/1995 | Waynant | 128/843 |
| 5,489,295 A | 2/1996 | Piplani et al. | |
| 5,499,995 A | 3/1996 | Teirstein | |
| 5,514,176 A | 5/1996 | Bosley, Jr. | |
| 5,545,210 A | 8/1996 | Hess et al. | 623/1 |
| 5,601,593 A | 2/1997 | Freitag | 606/198 |
| 5,601,600 A * | 2/1997 | Ton | 606/26 |
| 5,669,933 A | 9/1997 | Simon et al. | |
| 5,766,203 A * | 6/1998 | Imran | 606/194 |
| 6,145,505 A | 11/2000 | Nikolchev et al. | |
| 6,176,240 B1 * | 1/2001 | Nikolchev | 128/830 |
| 6,187,027 B1 * | 2/2001 | Mariant | 606/151 |
| 6,526,979 B1 | 3/2003 | Nikolchev et al. | |
| 6,634,361 B1 | 10/2003 | Nikolchev et al. | |
| 6,679,266 B1 | 1/2004 | Nikolchev et al. | |
| 6,684,884 B1 | 2/2004 | Nikolchev et al. | |
| 6,705,323 B1 | 3/2004 | Nikolchev et al. | |
| 6,709,667 B1 | 3/2004 | Lowe et al. | |
| 6,763,833 B1 | 7/2004 | Khera et al. | |
| 6,871,650 B1 | 3/2005 | Nikolchev et al. | |
| 2002/0020417 A1 | 2/2002 | Nikolchev et al. | |
| 2002/0029051 A1 | 3/2002 | Callister et al. | |

FOREIGN PATENT DOCUMENTS

| | | |
|---|---|---|
| EP | 1 199 049 | 4/2002 |
| WO | WO 90/09158 | 8/1990 |
| WO | WO 93/06884 | 4/1993 |
| WO | WO 94/24944 | 11/1994 |
| WO | WO 96/40024 | 12/1996 |
| WO | WO 99/15116 | 4/1999 |

OTHER PUBLICATIONS

A. Thurmond, MD, "Transcervical fallopian tube catheterization," Seminars in Interventional Radiology, vol. 9 (No. 2), p. 80-86, (Jun. 1992).

T. Schmitz-Rode, MD, et al., "Self-expandable spindle for transcatheter vascular occlusion: in vivo experiments," Radiology, vol. 188 (No. 1), p. 95-100, (Jul. 1993).

Benassi, John M. et al., "Conceptus' Amended Answer to Ovion's Complaint, Affirmative Defenses and Counterclaims" pp. 1-12, mailed on Sep. 27, 2002.

Benassi, John M. et al., "First Amendment Complaint for (1) Declaratory Judgment of Patent Non-Infringement, Invalidity and Unenforceability; (2) False Advertising Under 15 U.S.C. § 1125(A); (3) Trade Libel; (4) Unfair Competition Under Common Law and Cal. B&P § 17200 et seq.; (5) Unjust enrichment; and (6) Constructive Trust Demand for Jury Trial" pp. 1-19, dated Jun. 13, 2002.

International Search Report for PCT/US2005/003185, mailed May 2, 2005.

Written Opinion of the International Searching Authority for PCT/US2005/003185, mailed May 2, 2005.

International Search Report for PCT/US2005/003310, mailed May 2, 2005.

Written Opinion of the International Searching Authority for PCT/US2005/003310, mailed May 2, 2005.

Written Opinion of the International Searching Authority for PCT/US2003/41275, mailed Apr. 25, 2005.

Declaration of Steven Bacich in Support of Conceptus' Motion for Summary Judgment of Invalidity in View of Conceptus, Inc.'s '979 Patent.

Docket for Civil Action No. C 02 1968 MHP (United States District Court for the Northern District of California).

Docket for Civil Action No. C 02 3884 MHP (United States District Court for the Northern District of California).

First Amended Complaint For (1) Declaratory Judgment Of Patent Non-Infringement, Invalidity And Unenforceability; (2) False Advertising Under 15 U.S.C. § 1125(A); (3) Trade Libel; (4) Unfair Competition Under Common Law And Cal. B&P § 17200 Et. Seq.: (5) Unjust Enrichment; and (6) Constructive Trust.

Defendants' Request, Pursuant To Civil Local Rule 7-10(b), For Leave To File A Motion To Dismiss Before The Initial Case Management Conference, Conceptus' Amended Answer To Ovion's Complaint, Affirmative Defenses And Counterclaims.

Ovion's Reply To Amended Counterclaims Of Conceptus.

First Amended Complaint For Willful Patent Infringement, Fraud And Misrepresentation, Misappropriation, Unjust Enrichment, Unfair Business Practices, Trade Libel, Slander Of Title, Monopolization, Attempt To Monopolize And Sham Litigation.

Conceptus' Second Amended Answer, Affirmative Defenses And Counterclaims For: (1) Declaratory Judgment Of Non-Infringement; (2) Declaratory Judgment Of Unenforceability; (3) Declaratory Judgment Of Invalidity; (4) Correction Of Inventorship Of '052 Patent Under 35 U.S.C. § 256; (5) Correction Of Inventorship Of '116 Patent Under 35 U.S.C. § 256; (6) Fraud And Deceit; (7) Trade Libel; (8) Slander Per Se: (9) Libel; (10) Unfair Competition; And, (11) Slander Of Title.

Joint Claim Construction And Prehearing Statement Pursuant To Patent Local Rule 4-3.

Stipulation And Order Of Dismissal.

Ovion's Response to Conceptus' Interrogatories Nos. 2-4, 6-10, and 12-13.

Ovion's Corrected Disclosure of Asserted Claims and Preliminary Infringement Contentions.

Ovion's Corrected Supplemental Statement Regarding Dates of Invention.

Ovion's Second Supplemental Statement Regarding Dates of Invention.

Letter from L. Hansen to Judge Patel.

Letter from J. Benassi to Judge Patel.

Letter from L Hansen to Judge Patel.

Letter from J. Benassi to Judge with declarations of E. Brann and A. Khera.

Letter from E. Brann to Judge Patel with signed declaration of A. Khera.

Letter from L. Hansen to Judge Patel, enclosing for submission on behalf to Ovion its First Amended Complaint.

Conceptus' Motion for Summary Judgment of Invalidity of the Asserted '116 Patent Claims in View of Conceptus, Inc.'s '979 Patent.

Ovion's Motion To Change Time for Conceptus's Inappropriate Summary Judgment Motions.

Declaration of Leland G. Hansen In Support Of Ovion's Motion To Change Time, with Exhibits 1-8.

Notice of Opposition (Australian Patent Application No. 769576).

Statement of Grounds and Particulars (Australian Patent Application No. 769576).

Declaration of Kathryn Tunstall (Australian Patent Application No. 769576).

Declaration of Julian Nikolchev (Australian Patent Application No. 769576).

Declaration of Dr. Gabor Thomas Kovacs (Australian Patent Application No. 769576).

Declaration of Dr. John F. Kerin (Australian Patent Application No. 769576).

Second Declaration of Dr. John F. Kerin (Australian Patent Application No. 769576).

* cited by examiner

CONTRACEPTIVE SYSTEM AND METHOD OF USE

FIELD OF INVENTION

This invention relates to the field of contraceptive and sterilization devices and more particularly to reversible contraceptive devices and the methods of using such devices.

BACKGROUND OF THE INVENTION

Conventional contraceptive strategies generally fall within three categories: physical barriers, drugs and surgery. While each have certain advantages, they also suffer from various drawbacks. Barriers such as condoms and diaphragms are subject to failure due to breakage and displacement. Drug strategies, such as the pill and Norplant™, which rely on artificially controlling hormone levels, suffer from known and unknown side-effects from prolonged use. Finally, surgical procedures, such as tubal ligation and vasectomy, involve the costs and attendant risks of surgery, and are frequently not reversible. Thus, there remains a need for a safe, effective method of contraception, particularly a non-surgical method which is reversible.

SUMMARY OF THE INVENTION

The present invention is directed to a contraceptive or sterilization system for occluding a reproductive tract or lumen to prevent the passage of reproductive cells through the tract or lumen. The invention includes an occluding member expandable within the body lumen from a first configuration suitable for introduction into the body lumen to a second larger configuration to facilitate securing the expanded occluding member to at least a portion of a wall which defines the reproductive body lumen. The invention also includes means to facilitate securing the expanded occluding member to the wall of the body lumen and means to contract the expanded occluding member and the wall portion secured to the occluding member to occlude the reproductive body lumen sufficiently to prevent the passage of reproductive cells therethrough.

One presently preferred embodiment of the invention comprises a reversible contraceptive system which can be used to occlude either the fallopian tubes of a female patient, the vas deferens of a male patient or other reproductive tract. A key feature of the contraceptive system is a occluding member which is first secured to the wall defining the reproductive tract in an expanded condition and then is collapsed to smaller transverse cross-sectional dimensions to cause the collapse of the secured portion of the wall and thereby block the vessel passageway to prevent the passage of reproductive cells. The occluding member may be reopened by any number of suitable means. For example, by collapsing the occluding member about a plug or mandrel which can be left in place to effectively blocking the passageway until the patient wishes to reverse the procedure. The plug can be removed by suitable means such as conventional laparoscopic or other instruments to reopen the passageway. A balloon dilatation catheter may be used to further expand the opening once the plug is removed Other ways of reopening the reproductive lumen include leaving the proximal portion of the occluding member open when the member is collapsed so that an expandable member such a balloon on a catheter can be inserted and expanded. By means of a series of expansions and stepped advancements, the entire passageway can be reopened.

Preferably, the occluding member comprises a tubular member formed from a shape-memory alloy material and has a primary configuration which is relatively small in transverse dimensions to facilitate the insertion of the member into the desired body lumen. Once in place, the occluding member is then expanded to a second configuration with transverse dimensions roughly corresponding to or slightly larger than the body lumen so that the occluding member can be secured to the wall defining the body lumen. With the open, lattice-like framework of the occluding member expanded within the body lumen, endotherlialization through the open structure secures the occluding member to the wall defining the body lumen. By heating the occluding member formed of shape-memory alloy material to a temperature at or above the transition temperature of the shape-memory material, it transforms to a remembered closed or collapsed configuration which causes the wall secured to the occluding member to close down so that the passageway therethrough is occluded. The occluding member may be delivered to the desired location within the body lumen by suitable means such as a conventional balloon catheter similar to those used for delivering stents, aortic grafts and various types of prosthesis.

In one presently preferred embodiment, the occluding member has an open or lattice-like framework so that the growth of endothelial tissue through the openings of lattice-like framework so as to interconnect the occluding member and the wall of the body lumen. The surface of the occluding member may be treated to promote the endothelialization.

Once the occluding member is implanted into the body lumen and it has been sufficiently endothelialized to secure it to the body wall (which may take a week or more), it may be activated by warming the occluding member to a temperature at or above the transition temperature of the shape-memory material so it may revert to its remember constricted shape. Since the endotheliaization has secured the occluding member to the wall of the body lumen, the contraction of the occluding member to its remembered collapsed shape, causes the wall defining the body lumen to collapse along with the occluding member, effectively blocking the passageway. Alternatively, a plug may be located within the interior of the occluding member prior to heat activation so that the occluding member collapses onto the plug to block the lumen.

The occluding member may be mounted onto the exterior of a balloon of a dilatation balloon catheter in the first configuration with small transverse dimensions, and then be introduced and positioned within the region of the reproductive lumen to be occluded. The balloon is inflated to expand the occluding member, preferably with the outer diameter slightly larger than the inner dimensions of the reproductive lumen to which it is secured. The occluding member will remain in the open configuration until heated to a temperature at or above its martensite to austenite transition temperature which causes it to revert to its collapsed state. If the occluding member is collapsed about a plug, the plug may be extracted to reopen the passageway when the patient wishes to become fertile again.

The present invention provides effective sterilization or contraception for both males and females and importantly it is easily reversed. Moreover, the implantation and activation of the occluding member as well as the subsequent restoration of vessel patency requires easily used minimally invasive devices such as catheters, guidewires, guiding catheters and the like. These and other advantages of the invention

DETAILED DESCRIPTION OF THE INVENTION

Figure 1:
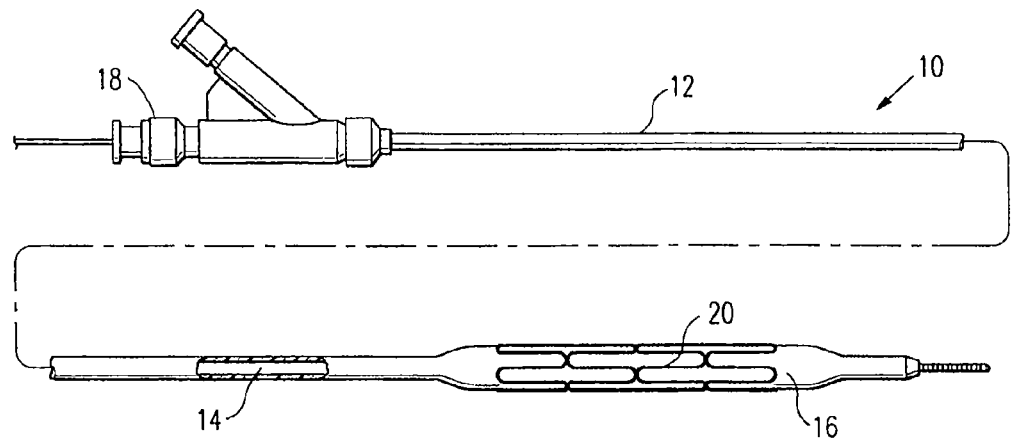
FIG. 1 illustrates a catheter with an occluding member embodying features of the invention mounted on an expandable member on a distal section of the catheter.

FIG. 1 illustrates a catheter 10 useful in the practice of the invention, which comprises an elongated shaft 12 having an inflation lumen 14 which is in fluid communication with inflatable member 16 mounted on a distal section of the catheter shaft and adapter 18. Occluding member 20, a self-supporting metallic member of shape-memory material, closely conforms to the diameter of the uninflated inflatable member 16 to facilitate introduction into the desired body lumen. Occluding member 20 is formed so that it has a remembered collapsed configuration with relatively small transverse dimensions. The occluding member 20 may be deformed to facilitate mounting onto the inflatable member 16 and is expanded by the inflatable member to an open expanded configuration within a body lumen. Upon heating to a transition temperature it will revert to the remembered configuration. In this embodiment the occluding member 20 has an open, lattice-type structure facilitating endothelialization which secures the occluding member to the wall defining the body lumen. Preferably, occluding member 20 can be deformed to an expanded diameter, preferably equal to or slightly larger than the dimensions of the body lumen within which the occluding member is to be disposed. For disposition within a female patient's fallopian tubes the expanded transverse dimensions should be about 0.1 mm to about 5 mm.

Figure 2:
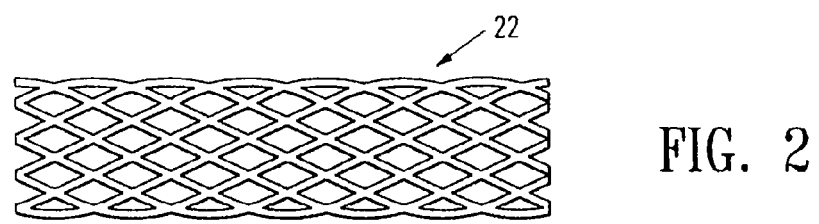
FIGS. 2 and 3 show one embodiment of the occluding member in expanded and contracted or closed configurations respectively.
Figure 3:
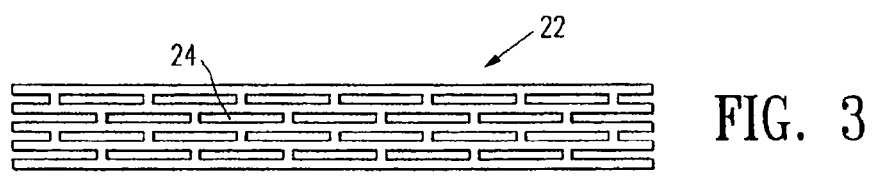
Figure 4:
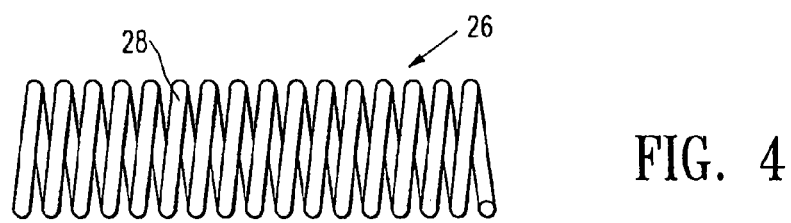
FIGS. 4 and 5 show another embodiment of the occluding member in expanded and closed configurations respectively.
Figure 5:
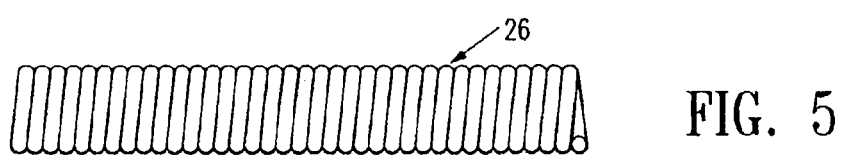
Figure 6:
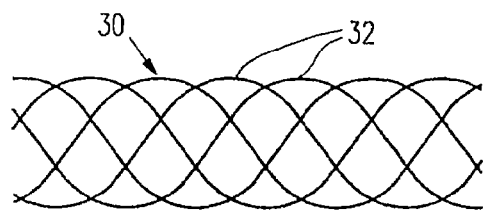
FIGS. 6 and 7 show yet another embodiment of an occluding member in expanded and closed configurations respectively.
Figure 7:
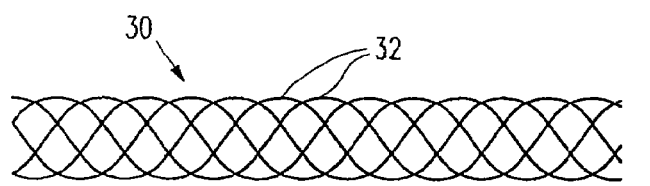
Figure 8:
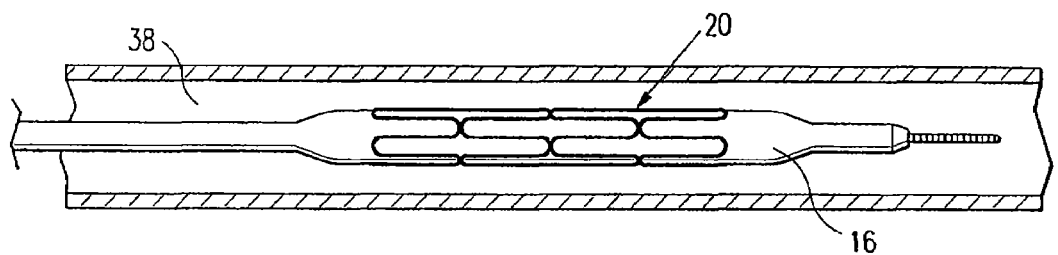
FIG. 8 depicts the occluding member on a delivery catheter as shown in FIG. 1 within a reproductive tract or lumen.

The occluding member may have a number of suitable configurations as shown in schematically in FIGS. 2–7. FIG. 2 illustrates occluding member 22 in an open configuration and FIG. 3 its relatively small dimensioned configuration for introduction and advancement into the patient's body lumen. Occluding member 22 may be constructed from a length of shape memory hypodermic tubing. Slots 24 cut into the wall of the tubing allow expansion of the occluding member into an open configuration as shown in FIG. 2. Likewise, in FIGS. 4 and 5, occluding member 26 is a coil 28 of shape-memory wire or ribbon. FIGS. 6 and 7 show occluding member 30, which comprises a braided tube of shape-memory wire or ribbon 32. Finally, in FIGS. 1 and 8 occluding member 20 comprises a number of closed sinusoidal rings of shape-memory wire or ribbon and is mounted onto an inflatable member 16 of catheter 10.

Figure 9:
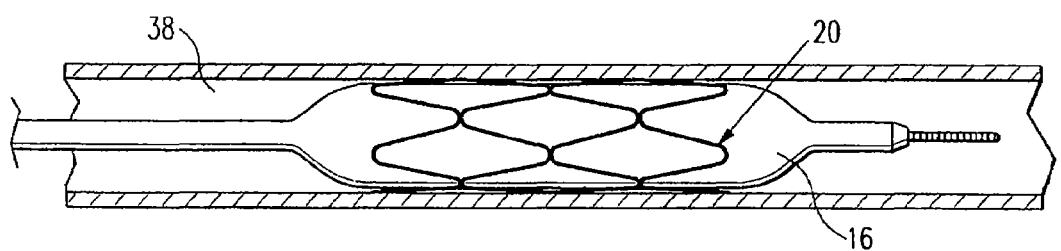
FIG. 9 illustrates the expansion of the occluding member within the reproductive tract or lumen.

Inflation of inflatable member 16 expands occluding member 20 in a reproductive tract 38 to an open, relatively large diameter configuration as shown in FIG. 9.

In each of these embodiments, the shape memory material of the occluding member should have a transition temperature sufficiently above the normal variation of human body temperature to prevent accidental activation which might prematurely collapse the occluding member. On the other hand, the transition temperature should be high enough so that thermal activation of the occluding member does not cause undesirable thermal damage to the surrounding tissue. The shape memory-material is preferably a shape memory, nickel-titanium alloy such as NITINOL and preferably has a transition temperature of between about 43° C. to about 70° C.

In each of the embodiments described above, certain conventional refinements may be employed. For example, the surface of the occluding member's framework may be designed to facilitate endothelial growth. Such modifications generally comprise providing the occluding member with an open or lattice-like framework to promote endothelial growth into as well as around the member to ensure it secure attachment to the wall of the body lumen. Suitable surface techniques include EDM machining, laser drilling, photo etching, scintering and the like. Additionally, increasing the surface area of the occluding member can also provide greater adhesion for the endothelial tissue. Suitable surface treatments include plasma etching, sand blasting, machining and other treatments to roughen the surface. In other embodiments, the shape-memory material may be coated or seeded to spur endothelialization. For example, the occluding device can be coated with a polymer having impregnated therein a drug, enzyme or protein for inducing or promoting endothelial tissue growth. In yet another refinement, the occluding member could be plated with or otherwise incorporate copper to produce an inflammatory response in the tissue of the wall defining the body lumen, which further contributes to the obstruction of the lumen. Other inflammatory materials my be suitable as well. For example, the occluding member could be radioactive, emitting alpha, beta or gamma particles.

Figure 10:
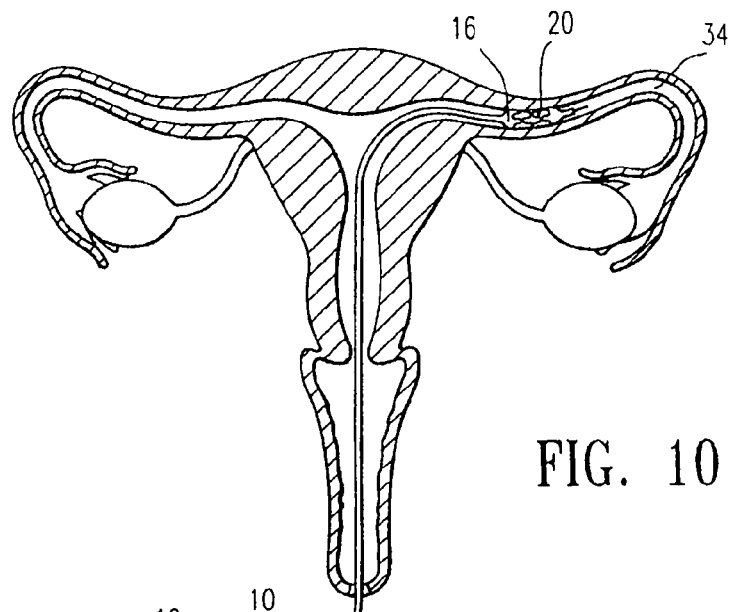
FIG. 10 illustrates the female reproductive anatomy and shows the occluding member positioned within one of the patient's fallopian tubes.
Figure 11A:
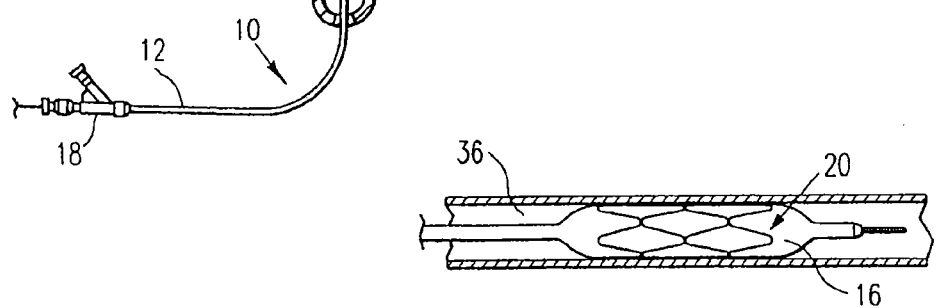
FIG. 11 illustrates the male reproductive anatomy and depicts an expanded occluding member within a vas deferens of a male patient.
Figure 11:
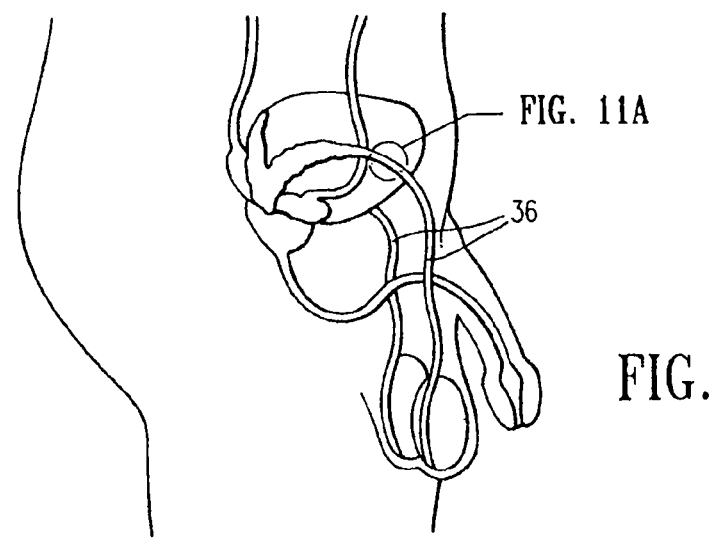
Figure 12:
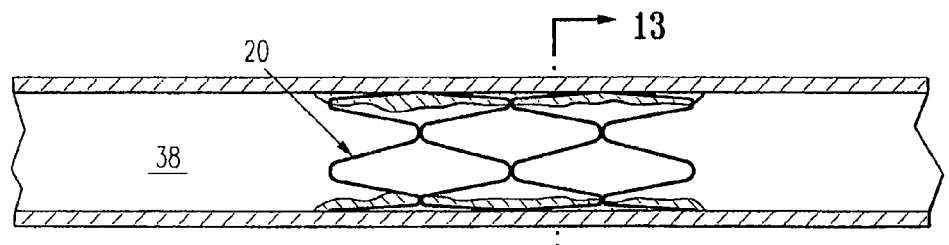
FIG. 12 illustrates the occluding member secured to the wall of the reproductive tract by epithelial tissue.

The practice of the invention comprises the following general steps. An occluding member 20 having relatively small transverse dimension is mounted onto the exterior of balloon 16 of catheter 10 as shown in FIG. 1. The catheter 10 is advanced under fluoroscopic or endoscopic visualization until occluding member 20 is positioned within one of the female patient's fallopian tubes 34, as shown in FIG. 10. Inflation fluid is introduced through adapter 18 to inflate inflatable member 16. As shown in FIGS. 9–10, inflation of inflatable member 16 expands occluding member 20 to an open configuration and lodging it in body lumen 38. Catheter 10 is removed, leaving the expanded occluding member 20 implanted in body lumen 38 as shown in FIG. 12. Another expandable member is delivered to the patient's other fallopian tube and expanded therein in the same manner. Alternatively, the occluding member may be expanded into positioned within the vas deferens 36 of a male patient as shown in FIG. 11 to provide male contraception using the same procedures.

Figure 13:
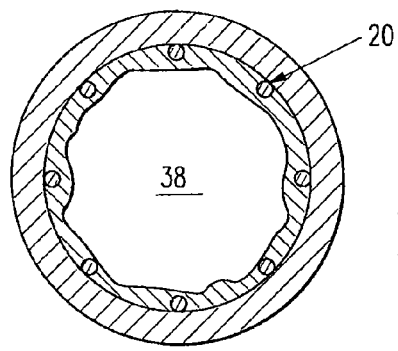
FIG. 13 is a transverse cross-sectional view of the expanded epithelized occluding member as shown in FIG. 12 taken along the lines 13—13.
Figure 14:
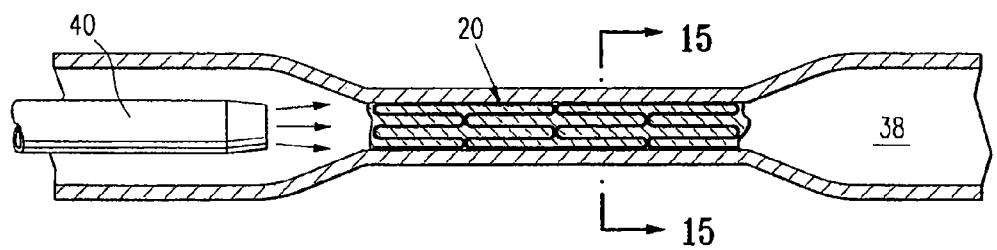
FIG. 14 shows the occluding member in a collapsed state after being activated by warmed saline.

Over a period of a week or more epithelial cells lining the lumen will proliferate, growing around the open framework of occluding member 20 as shown in FIGS. 12 and 13 thereby securing the wall defining the body lumen 38 to the expanded occluding member 20. After the expanded occluding member 20 is sufficiently epithelized within the patient's reproductive tract 38, it is thermally activated to return it to its remembered collapsed configuration. The occluding member may be activated by several means, including warmed fluid, RF energy, laser energy, or other suitable energy sources. A suitable activation system is shown in FIG. 14 where the distal end of catheter 40 is positioned adjacent to the occluding member 20, saline fluid somewhat above the transition temperature is introduced to bathe occluding member 20, raising its temperature to the transition point or higher, causing occluding member 20 to collapse to its closed, reduced-diameter configuration. The layer of epithelial tissue that forms within the lattice-like structure of the occluding member helps block and seal the lumen so as to prevent the passage of reproductive cells, eggs or sperm cells.

Figure 16:
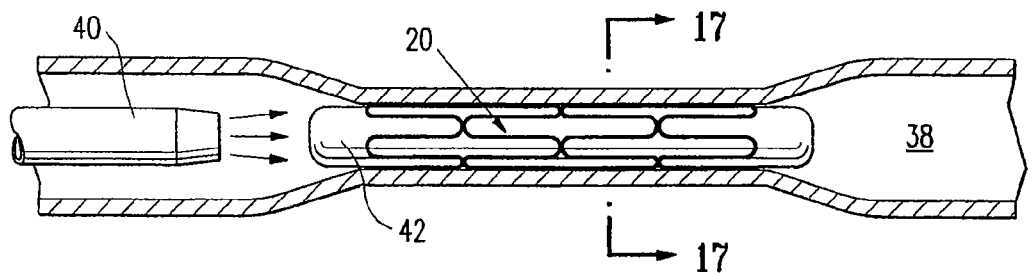
FIG. 16 is similar to FIG. 14 and illustrates the occluding member collapsed about an elongated removable plug or mandrel.
Figure 17:
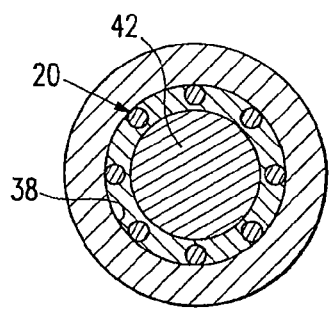
FIG. 17 illustrates a transverse cross section of the occluding member shown in FIG. 16, taken along line 17—17.
Figure 18:
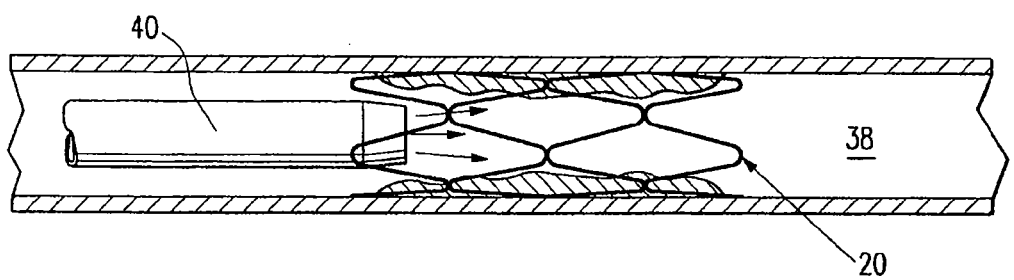
FIG. 18 shows the occluding member being activated in a location distal to the proximal extremity thereof in order to keep the proximal end partially open to facilitate reopening the passageway.

In an alternative embodiment of the invention is shown in FIG. 16 where a plug 42 is positioned inside occluding member 20 in the expanded condition so that upon activation the occluding member 20 collapses onto plug 42, blocking the lumen 38. The plug is preferably formed from an inert material such as a fluoropolymer, e.g. PTFE. Other suitable materials include high density polyethylene and silicone rubber. A number of modifications to the plug may also be suitable. For example, the plug could be used as a drug delivery device, similar to the Norplant™ device. The plug could also be used to provoke an inflammatory response as described above to augment the occlusion of the lumen. In such embodiments, plug 42 preferably has an outer diameter from about 0.25 mm to about 4 mm. The plug 42 may also have holes, deep grooves or which help to preserve at least part of the natural lining of the reproductive tract.

Figure 15:
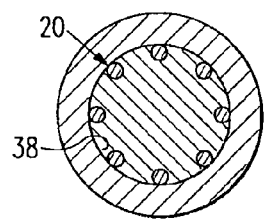
FIG. 15 is a transverse cross-sectional view of the collapsed occluding member as shown in FIG. 14 taken along the lines 15—15.

The occlusion of the lumen may be reversed simply by removing the plug 42. If a passageway larger than passageway left by the removed plug 42 is desired, a balloon catheter can be advanced within the body lumen until the balloon is within the lumen left by the removal of the plug and then the balloon on the catheter is inflated to expanded the occluding member 20, deforming it into an open configuration. It may be desirable when activating the expanded occluding member to the collapsed configuration to leave the proximal end of the occluding member somewhat open or in an expanded condition to facilitate the introduction of dilatation balloon on a catheter to facilitate the opening of the body lumen. As shown in FIG. 15, the catheter 40 used to activate the occluding member may be positioned within the proximal end of the occluding member, so that the proximal end is unable to completely revert to its closed configuration. The reproductive tract could be subsequently close should contraception again be desired by heating the occluding member 20 so as to activate the transformation thereof to the collapsed configuration.

In embodiments of the invention employing the plug 40, various other strategies are suitable to reverse the occlusion. For example, the plug 40 can simply be removed, restoring the lumen 38 to patency. Alternatively, the plug 40 may be hollow with a removable core (not shown). This core may be formed from a softer material, such as silicone, or could be threaded, in order to facilitate its removal. Similarly, the plug itself may be threaded so that removal would comprise a twisting motion, minimizing the stress on the tissue in which the occluding member is located.

In still other embodiments, mechanical, adhesive or other means may be employed to secure the expanded occluding member 20 to the vessel wall defining the reproductive passageway 38. For example, the means to secure a stent or prosthetic device to an aortic or arterial wall described in U.S. Pat. No. 4,140,126; U.S. Pat. No. 4,562,596; U.S. Pat. No. 4,577,631; U.S. Pat. No. 4,787,899; U.S. Pat. No. 5,104,399; U.S. Pat. No. 5,167,614; U.S. Pat. No. 5,275,622; U.S. Pat. No. 5,456,713; and U.S. Pat. No. 5,489,295 may be used with the present invention to interconnect the wall defining the reproductive tract and the expandable member. These patents are incorporated herein in their entireties by reference.

Figure 19:
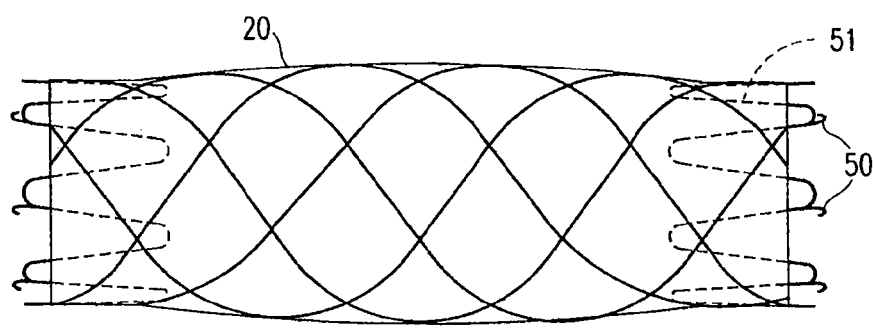
FIG. 19 shows an embodiment of the occluding member having hooks.

FIG. 19 illustrates one embodiment of invention having hook members 50 on the occluding member 20. The hook members 50 spread radially outward from the longitudinal axis of the occluding member 20, so that they contact the wall defining the reproductive tract as the occluding member expands therein. Thus, the hook members 50 become embedded in the wall defining the reproductive tract to anchor the occluding member 20 therein. In the embodiment illustrated in FIG. 19, the hook members 50 are located on the distal and proximal ends of the occluding member 20, although other suitable configurations exist including hook members 50 which are disposed along all or part of a length of the occluding member 20. A variety of suitable means may be used to attach the hook members 50 to the occluding member 20, such as welding or brazing. Alternatively, as shown, they are attached to a connecting member 51 which is attached to the occluding member 20.

Various modifications and improvements may be made to the present invention without departing from the scope thereof. For example, a mechanical expandable member such as described in U.S. Pat. No. 4,585,000, which is incorporated herein by reference, may be used to expand the expandable member within the reproductive tract to engage the wall thereof. Moreover, although individual features of embodiments of the invention may be shown in some of the drawings and not in others, those skilled in the art will recognize that individual features of one embodiment of the invention can be combined with any or all the features of one or more of the other embodiments.

What is claimed is:

1. A contraceptive device, comprising a tubular body which has a longitudinal axis, which is at least in part configured to be radially expanded about the longitudinal axis within a lumen of a patient's reproductive system from a first configuration to a second configuration having larger transverse dimensions than the first configuration, which has an open framework in the expanded configuration for ingrowth of tissue cells for securing the expanded portion of the tubular body to a wall portion of the patient's reproductive system lumen, which has at least one open end and which has a member at least partially within an interior portion thereof configured for tissue growth.

2. The contraceptive device of claim 1 wherein the member within the tubular body is a plug.

3. The contraceptive device of claim 2 wherein the surface of the plug is roughened to provide tissue adhesion.

4. The contraceptive device of claim 1 wherein the member at least partially within the tubular body promotes tissue growth including an inflammatory response.

5. The contraceptive device of claim 1 wherein the tubular member is formed of a thin walled metallic tube having a pattern of openings.

6. The contraceptive device of claim 1 wherein the tubular member is formed of a helical wire.

7. The contraceptive device of claim 1 wherein the tubular member is formed of a braided wire tube.

8. The contraceptive device of claim 1 wherein the tubular body is configured at least in part to retain substantially the second tubular configuration for sufficient time for tissue growth to epithelialize at least an expanded portion of the tubular body.

9. The contraceptive device of claim 1 wherein at least part of the tubular body is configured to have outer transverse dimensions in the expanded second configuration which substantially conform to inner transverse dimensions of the patient's reproductive lumen at an expansion site in the reproductive lumen.

10. A contraceptive device, comprising
    a) a tubular body which has a longitudinal axis, which is at least in part configured to be radially expanded about the longitudinal axis within a lumen of a patient's reproductive system from a first configuration to a second configuration having larger transverse dimensions than the first configuration to facilitate securing a least a portion of the tubular body to a wall portion defining at least in part a lumen of a patient's reproductive system, which has at least one open end and which has an open framework in the expanded configuration facilitating the ingrowth of tissue cells; and
    b) a member at least partially within the tubular body which is configured for tissue growth.

11. The contraceptive device of claim 10 wherein the tubular member is formed of a thin walled metallic tube having a pattern of openings.

12. The contraceptive device of claim 10 wherein the tubular member is formed of a helical wire.

13. The contraceptive device of claim 10 wherein the tubular member is formed of a braided wire tube.

14. The contraceptive device of claim 10 wherein the tubular body is configured to retain substantially the second tubular configuration at least in part for sufficient time for tissue growth to epithelialize at least an expanded portion of the tubular body.

15. The contraceptive device of claim 10 wherein at least part of the tubular body is configured to have outer transverse dimensions in the expanded second configuration which substantially conform to inner transverse dimensions of the patient's reproductive lumen at an expansion site in the reproductive lumen.

16. A contraceptive device for deployment in a female patient's fallopian tube, comprising:
    a) a tubular body which has a longitudinal axis, which at least in part is configured to be radially expanded about the longitudinal axis within the patient's fallopian tube from a first configuration to a second configuration having larger transverse dimensions than the first configuration to facilitate securing a least a portion of the expanded tubular body to a wall portion defining at least in part a lumen of the female patient's fallopian tube, which has at least one open end and which has an open framework in the expanded configuration facilitating ingrowth of tissue cells; and
    b) a member at least in part within the tubular body which is configured for tissue growth.

17. The contraceptive device of claim 16 wherein the tubular body is configured at least in part to retain substantially the second tabular configuration for sufficient time for tissue growth to epithelialize at least an expanded portion of the tubular body.

18. The contraceptive device of claim 16 wherein the tubular body is configured to substantially conform to the inner transverse dimensions of the patient's fallopian tube in the second tubular configuration and to at least in part retain substantially the second tubular configuration for sufficient time for tissue growth to epithelialize at least an expanded portion of the tubular body.

19. A contraceptive device for deployment in a lumen of a male patient's reproductive system, comprising:
    a) a tubular body which has a longitudinal axis, which at least in part is configured to be radially expanded about the longitudinal axis within the patient's lumen from a first configuration to a second configuration having larger transverse dimensions than the first configuration to facilitate securing a least a portion of the expanded tubular body to a wall portion defining at least in part the patient's lumen, which has at least one open end and which has an open framework in the expanded configuration facilitating ingrowth of tissue cells; and
    b) a member at least in part within the radially expandable tubular body which is configured for tissue growth.

20. A method of human contraception comprising
    a) providing a contraceptive device comprising a tubular body having at least one open end and a member which is configured for tissue growth which is disposed at least partially within the tubular body;
    b) inserting within a lumen of a patient's reproductive system at least a portion of the contraceptive device including at least part of the tubular body and at least part of the tissue growth member, and
    c) within a region of the patient's reproductive lumen, radially expanding at least a tubular portion of the tubular body about a longitudinal axis from a first configuration to a second configuration having outer transverse dimensions which are larger than outer transverse dimensions in the first configuration and which substantially conform to the inner transverse dimensions of the patient's reproductive lumen in the region where the tubular portion is expanded.

21. The method of claim 20 wherein occlusion of the reproductive lumen is facilitated by tissue growth promoted by the tissue growth member.

22. The method of claim 20 wherein the tissue growth includes an inflammatory response.

23. The method of claim 20 wherein contraception is aided by a contraceptive drug associated with the device.

24. The method of claim 20 wherein the tubular portion is expanded at least partially by self-expanding.

25. The method of claim 20 wherein the step of inserting at least a portion of the contraceptive device within the patient's reproductive lumen further comprises using a catheter to introduce at least the portion of the contraceptive device into the reproductive lumen.

26. The method of claim 20 wherein the expanded tubular portion is retained substantially in the second configuration within the patient's reproductive lumen.

27. The method of claim 26 wherein the expanded tubular portion is retained substantially in the second configuration within the patient's reproductive lumen for a period of at least seven days.

28. The method of claim 20 wherein at least part of the expanded tubular portion of the tubular body is secured by tissue ingrowth to a wall of the patient's reproductive lumen.

29. The method of claim 20 wherein the expanded tubular portion of the tabular body is contracted from the second configuration to a remembered configuration having smaller transverse dimensions than the second configuration.

30. The method of claim 20 wherein tissue growth surrounds the expanded tubular portion of the tubular body and at least a portion of the tissue growth member within the patient's reproductive lumen.

31. The method of claim 30 wherein the contraceptive device is secured to a portion of a wall forming the patient's reproductive lumen by tissue growth surrounding at least part of the expanded tubular portion of the tubular body within the reproductive lumen.

32. The method of claim 20 wherein the contraceptive device is secured to a portion of a wall fanning the patient's reproductive lumen.

33. The method of claim 20 wherein the radial expansion of the tubular portion of the tubular member to the second larger configuration secures at least the expanded tubular portion of the tubular body at an expansion site within the patient's reproductive lumen.

34. A human contraceptive device comprising:
a) a tubular body which has a longitudinal axis, which has at least a tubular portion that is configured to be radially expanded within a lumen of a patient's reproductive system about the longitudinal axis from a first configuration to a second configuration having outer transverse dimensions larger than outer transverse dimensions in the first configuration, which has at least one open end and which substantially conforms to inner transverse dimensions of the patient's reproductive lumen at an expansion site therein; and
b) a member which is configured for tissue growth and which is disposed at least partially within the tubular body.

35. The contraceptive device of claim 34 wherein the tubular portion is configured to have an open frame work in the second configuration.

36. The contraceptive device of claim 35 wherein the tubular portion is configured to be retained in the second configuration.

37. The contraceptive device of claim 35 wherein the tubular body is selected from the group consisting of a thin walled metallic tube having a pattern of openings, a helical wire tube, and a braided wire tube.

38. The contraceptive device of claim 34 wherein the tissue growth member is a plug with holes and grooves for tissue growth.

39. The contraceptive device of claim 34 wherein the tissue growth member comprises a plug.

40. The contraceptive device of claim 34 wherein the tubular body is configured to promote tissue growth including an inflammatory response.

41. The contraceptive device of claim 34 including a deliverable contraceptive agent.

42. The contraceptive device of claim 34 wherein the tubular body is formed at least in part of a nickel-titanium alloy.

43. The contraceptive device of claim 34 wherein the tissue growth member is configured to support tissue growth that contributes to occlusion of the reproductive lumen.

44. The contraceptive device of claim 34 wherein the tubular portion of the tubular body is at least partially self-expanding.

45. The contraceptive device of claim 34 wherein at least the tubular portion of the tubular body is configured to be retained substantially in the second expanded configuration within the patient's reproductive lumen for a period of at least seven days.

46. The contraceptive device of claim 34 wherein at least a portion thereof is configured to be secured by tissue ingrowth to a wall of the patient's reproductive lumen.

47. The contraceptive device of claim 34 wherein at least a part of the tabular portion of the tubular body is configured to contract from the second configuration to a remembered configuration having smaller transverse dimensions than the second configuration to facilitate occlusion of the patient's reproductive lumen.

48. The contraceptive device of claim 34 wherein the tubular portion of the tubular body and the tissue growth member are configured to provoke tissue growth that surrounds at least in part the expanded tubular portion of the tubular body and at least a portion of the tissue growth member within the patient's reproductive lumen to substantially occlude the reproductive lumen.

49. The contraceptive device of claim 34 wherein at least part of the tubular body is configured to be secured to a portion of a wall forming the patient's reproductive lumen.

50. The contraceptive device of claim 34 wherein the tubular portion of the tubular body is configured to be secured to a portion of a wall forming the patient's reproductive lumen by tissue growth.

51. The contraceptive device of claim 34 wherein the tubular portion of the tubular body is configured to be secured within the patient's reproductive lumen upon expansion to the second configuration.

52. A method of human contraception comprising:
a) providing a contraceptive device comprising a tubular body which has a longitudinal axis, which at least in part is configured to be radially expanded about the longitudinal axis within a patient's reproductive lumen from a first configuration to a second configuration having larger transverse dimensions than the first tubular configuration to facilitate securing a least a portion of the expanded tubular body to a wall portion defining at least in part the patient's lumen, which has at least one open end and which has an open framework in the expanded configuration facilitating ingrowth of tissue cells;
b) inserting within a lumen of a patient's reproductive system at least a portion of the contraceptive device including at least part of the tubular body; and
c) within a region of the patient's reproductive lumen, radially expanding at least a tubular portion of the tubular body about the longitudinal axis from the first configuration to the second configuration which substantially conforms to inner transverse dimensions of the patient's reproductive lumen in the region where the tubular portion is expanded and which facilitates tissue growth that surrounds at least in part the expanded tubular portion of the tubular body within the patient's reproductive lumen to substantially occlude the reproductive lumen.

53. A contraceptive device, comprising;
a) a tubular body which has a longitudinal axis, which is at least in part configured to be radially expanded about the longitudinal axis within a lumen of a patient's reproductive system from a first configuration to a second cylindrical tubular configuration having larger transverse dimensions tan the first configuration to facilitate securing a least a portion of the tubular body to a wall portion defining at least in part a lumen of a patient's reproductive system and which has an open framework in the expanded configuration facilitating the ingrowth of tissue cells; and
b) a member at least partially within the tubular body which is configured for tissue growth.

54. The contraceptive device of claim 53 wherein the tubular body is formed of a thin walled metallic tube having a pattern of openings.

55. The contraceptive device of claim 53 wherein the tubular body is formed of a helical coil.

56. The contraceptive device of claim 53 wherein the tubular body is formed of braided wire.

57. The contraceptive device of claim 53 wherein the tubular body has at least one open end.

58. The contraceptive device of claim 53 wherein the tubular body has an open proximal end and an open distal end.

59. A contraceptive device, comprising:
a) a tubular member comprises a coil member which has a longitudinal axis, which is at least in part configured to be radially expanded about the longitudinal axis within a lumen of a patient's reproductive system from a first configuration to a second configuration having larger transverse dimensions than the first configuration to facilitate securing a least a portion of the helical coil to a wall portion defining at least in part a lumen of a patient's reproductive system and which has an open framework in the expanded configuration facilitating the ingrowth of tissue cells; and
b) a member which is disposed at least partially within the helical coil and which is configured for tissue growth.

60. The contraceptive device of claim 59 wherein the helical coil has at least one open end.

61. The contraceptive device of claim 59 wherein the helical coil has an open proximal end and an open distal end.

62. The contraceptive device of claim 59 wherein the helical coil is formed of a single strand.

63. The contraceptive device of claim 59 wherein the helical coil has a cylindrical shape in the expanded configuration.

64. A contraceptive device for occluding a lumen of a patient's reproductive system, comprising:
a) an elongated tubular member which has a longitudinal axis, which is at least in part configured to be radially expanded about the longitudinal axis within a lumen of a patient's reproductive system from a first configuration to a second configuration having larger transverse dimensions than the first configuration to facilitate securing a least a portion of the tubular body to a wall portion defining at least in part a lumen of a patient's reproductive system, which has open proximal and distal ends and which has an open framework in the expanded configuration facilitating the ingrowth of tissue cells; and
b) a member which is disposed at least partially within the tubular member and which is configured for tissue growth.

65. A method of human contraception comprising
a) providing a contraceptive device comprising a coil member which has a longitudinal axis, which at least in part is configured to be radially expanded about the longitudinal axis within a patient's reproductive lumen from a first configuration to a second expanded configuration having larger transverse dimensions than the first tubular configuration to facilitate securing a least a portion of the expanded tubular body to a wall portion defining at least in part the patient's lumen, which has at least one open end and which has an open framework in the expanded configuration facilitating ingrowth of tissue cells;
b) inserting within a lumen of a patient's reproductive system at least a portion of the contraceptive device including at least part of the coil member; and
c) within a region of the patient's reproductive lumen, radially expanding at least a portion of the coil member about the longitudinal axis from the first configuration to the second configuration which substantially conforms to inner transverse dimensions of the patient's reproductive lumen in the region where the coil member is expanded and which facilitates tissue growth that surrounds at least in part the expanded tubular portion of the tubular body within the patient's reproductive lumen to substantially occlude the reproductive lumen.

66. The method of claim 65 wherein the tissue growth substantially occludes the patient's reproductive lumen.

67. The method of claim 65 wherein the coil member is substantially in the form of a cylinder in the expanded configuration.

68. The method of claim 65 wherein a member configured for tissue growth is disposed at least partially within the coil member.

69. The method of claim 68 wherein the member configured for tissue growth is a plug.

70. A contraceptive device comprising a tubular coil member which has a longitudinal axis, which is at least in part configured to be radially expanded about the longitudinal axis within a lumen of a patient's reproductive system from a first configuration to a second configuration having larger transverse dimensions than the first configuration to facilitate securing a least a portion of the coil member to a wall portion defining at least in part a lumen of a patient's reproductive system and which has an open framework in the expanded configuration facilitating the ingrowth of tissue cells.

71. The contraceptive device of claim 70 wherein a member configured for tissue growth is disposed at least partially within the tubular coil member.

72. The contraceptive device of claim 71 wherein the member configured for tissue growth is a plug.

* * * * *

UNITED STATES PATENT AND TRADEMARK OFFICE
CERTIFICATE OF CORRECTION

PATENT NO.         : 7,073,504 B2
APPLICATION NO. : 08/770123
DATED              : July 11, 2006
INVENTOR(S)        : Callister et al.

It is certified that error appears in the above-identified patent and that said Letters Patent is hereby corrected as shown below:

At Col. 7, Line 45, please delete "a" and insert --at--.

At Col. 8, Line 11, please delete "securing a" and insert --securing at--.

At Col. 8, Line 38, please delete "securing a" and insert --securing at--.

At Col. 10, Line 56, please delete "securing a" and insert --securing at--.

At Col. 11, Line 15, please delete "tan" and insert --than--.

At Col. 11, Line 16, please delete "securing a" and insert --securing at--.

At Col. 11, Line 42, please delete "securing a" and insert --securing at--.

At Col. 12, Line 2, please delete "securing a" and insert --securing at--.

At Col. 12, Line 18, please delete "securing a" and insert --securing at--.

At Col. 12, Line 53, please delete "securing a" and insert --securing at--.

Signed and Sealed this

Seventeenth Day of October, 2006

JON W. DUDAS
*Director of the United States Patent and Trademark Office*